United States Patent
Luo et al.

(10) Patent No.: US 11,590,199 B2
(45) Date of Patent: Feb. 28, 2023

(54) USE OF AN ABC TRANSPORTER PEPTIDE INHIBITOR

(71) Applicant: HUNAN UNIVERSITY OF SCIENCE AND ENGINEERING, Hunan (CN)

(72) Inventors: Xiaofang Luo, Hunan (CN); Zuodong Qin, Hunan (CN); Meifeng Wang, Hunan (CN); Dongfang Tang, Hunan (CN)

(73) Assignee: HUNAN UNIVERSITY OF SCIENCE AND ENGINEERING, Yongzhou (CN)

( * ) Notice: Subject to any disclaimer, the term of this patent is extended or adjusted under 35 U.S.C. 154(b) by 0 days.

(21) Appl. No.: 17/324,053

(22) Filed: May 18, 2021

(65) Prior Publication Data
US 2021/0275626 A1   Sep. 9, 2021

(51) Int. Cl.
| | |
|---|---|
| *A61K 38/10* | (2006.01) |
| *A61K 31/337* | (2006.01) |
| *A61K 31/365* | (2006.01) |
| *A61K 31/475* | (2006.01) |
| *A61K 31/506* | (2006.01) |
| *A61K 31/704* | (2006.01) |
| *A61K 45/06* | (2006.01) |

(52) U.S. Cl.
CPC ............ *A61K 38/10* (2013.01); *A61K 31/337* (2013.01); *A61K 31/365* (2013.01); *A61K 31/475* (2013.01); *A61K 31/506* (2013.01); *A61K 31/704* (2013.01); *A61K 45/06* (2013.01)

(58) Field of Classification Search
None
See application file for complete search history.

(56) References Cited

U.S. PATENT DOCUMENTS

2009/0208493 A1    8/2009  Larson et al.
2019/0336568 A1 *  11/2019  Luo ........................ A61K 38/10

FOREIGN PATENT DOCUMENTS

| CN | 103520146 A | 1/2014 | |
|---|---|---|---|
| CN | 110478487 A | 11/2019 | |
| WO | WO-2018086516 A1 * | 5/2018 | ........... A23K 20/147 |

OTHER PUBLICATIONS

Ji et al. "VS-4718 Antagonizes Multidrug Resistance in ABCB1- and ABCG2-Overexpressing Cancer Cells by Inhibiting the Efflux Function of ABC Transporters," Frontiers in Pharmacology 2018 vol. 9, Article 1236, pp. 1-12 (Year: 2018).*
Sun et al. "Role of ABC transporters in cancer chemotherapy," Chinese Journal of Cancer 2012, vol. 31, pp. 51-57 (Year: 2012).*

* cited by examiner

*Primary Examiner* — Christina Bradley

(57) ABSTRACT

Disclosed herein is a use of an adenosine triphosphate (ATP) binding cassette (ABC) transporter peptide inhibitor HX-12C. This disclosure also discloses a method of treating a tumor with multidrug resistance mediated by the ABC transporter using a combination of the peptide HX-12C shown in SEQ ID NO: 1 and an ABC transporter substrate chemotherapeutic drug. Moreover, this disclosure also provides a composition for treating a tumor with multidrug resistance mediated by an ABC transporter, consisting of the peptide HX-12C shown in SEQ ID NO: 1 and an ABC transporter substrate chemotherapeutic drug.

5 Claims, 8 Drawing Sheets
Specification includes a Sequence Listing.

Relative intensity of ABCC1

USE OF AN ABC TRANSPORTER PEPTIDE INHIBITOR

CROSS-REFERENCE TO RELATED APPLICATIONS

This application claims the benefit of priority from Chinese Patent Application No. 202010416610.5, filed on May 18, 2020. The content of the aforementioned application, including any intervening amendments thereto, is incorporated herein by reference in its entirety.

TECHNICAL FIELD

This application relates to oncotherapy, and more particularly to a use of an ATP-binding cassette (ABC) transporter peptide inhibitor.

BACKGROUND

In the tumor treatment, the occurrence of multidrug resistance is the most important factor causing the chemotherapy failure and tumor recurrence. The molecular mechanism of the tumor multidrug resistance is relatively complex, while it has been found that the high expression of the ATP-binding cassette transporter superfamily (ABC family) in tumor tissues is the main cause for the tumor multidrug resistance. As a main member in the ABC transporter family, ABCB1 and ABCC1 are highly expressed in a variety of tumor tissues, for example, ABCB1 is highly expressed in human oral epidermal cancer cells, colon cancer cells, liver cancer cells and prostate cancer cells; ABCC1 exhibits high expression in lung cancer cells, liver cancer cells, intestinal cancer cells and breast cancer cells. ABCB1 and ABCC1 can identify a variety of antitumor chemotherapeutics, and then pump chemotherapeutic drugs out of tumor cells using the energy released by ATP hydrolysis, so that the concentration of chemotherapeutic drugs in the tumor cells is reduced, and the efficacy of chemotherapeutic drugs is weakened or even disappears. Therefore, the combination of an ABC transporter inhibitor and traditional chemotherapeutic drugs to reduce or inhibit the expression of ABC transporter and increase the concentration of chemotherapeutic drugs in the drug-resistant tumor cells is considered as a clinically effective strategy to overcome ABC transporter-mediated multidrug resistance. However, the existing ABC transporter inhibitors are greatly limited in the clinical application due to poor selectivity, interaction with chemotherapeutic drug, and low safety. Therefore, it is of great significance to develop a novel ABC transporter inhibitor with high efficiency, low toxicity and strong selectivity to overcome the drug resistance of tumors.

Polypeptides are widely found in animal and plant tissues. Many polypeptides have special functions in organisms, and are collectively referred to as bioactive polypeptides. Recently, the bioactive polypeptides have been demonstrated to play an important role in many fields of life sciences, such as immune defense, reproduction control, tumorigenesis and anti-aging. Among the bioactive polypeptides, antimicrobial polypeptides (AMP) and antitumor polypeptides (APC) have been studied extensively. AMP refers to a class of polypeptide molecules secreted by a variety of organisms such as invertebrates, plants and animals, which can effectively kill foreign pathogens such as bacteria, fungi, viruses, etc., and are a part of the natural immune system of organisms. APC refers to a class of polypeptides that inhibit the growth and proliferation of tumor cells, and most of them are derived from AMP. Most AMP and APC have similar structural characteristics, that is, they are generally composed of 10-40 amino acids, and have positively charged polar amino acids and a certain proportion of non-polar amino acids, thus showing amphiphilicity. AMP and APC act very quickly, such that the tumor cells are not easy to develop drug resistance. In view of this, the polypeptides have become a research hotspot in the development of new drugs.

After the asymmetric distribution of phospholipids in tumor cell membranes is destroyed, phosphatidylethanolamine (PE) and phosphatidylserine (PS) appear in large quantities on the outer layer of the cell membrane. At this time, through the electrostatic attraction between the positively charged polar amino acids in the polypeptide chain and the negatively charged phospholipids (PS) on the surface of the tumor cell membrane, the polypeptide is aggregated on the surface of the tumor cell membrane. The aggregated polypeptide presents an α-helical structure, in which the hydrophobic amino acids on the non-polar side can extend into the inner layer of the cell membrane by hydrophobic interaction, thereby further exerting an antitumor effect by the mechanism of membrane lysis and non-membrane lysis. In the previous researches related to the drug resistance of tumors, polypeptides are generally used as anti-cancer agents. Although they have certain selectivity for tumor cells, they are also toxic to normal cells at an effective tumor-inhibiting concentration, which limit their clinical application.

SUMMARY

An object of this disclosure is to provide an application of a combination of an ABC transporter inhibitor and an ABC transporter substrate chemotherapeutic drug in the preparation of a drug for treating an ABC transporter-mediated multidrug resistance tumor.

The technical solutions of the present disclosure are described as follows.

In a first aspect, the present disclosure provides a method of treating a tumor with multidrug resistance in a subject in need thereof, comprising:

administering a peptide HX-12C (FFRKVLKLIRKIWR, as shown in SEQ ID NO: 1) to the subject.

In some embodiments, the multidrug resistance is mediated by an adenosine triphosphate (ATP)-binding cassette (ABC) transporter.

In some embodiments, the ABC transporter is ATP-binding cassette subfamily B member 1 (ABCB1) or ATP-binding cassette subfamily C member 1 (ABCC1).

In some embodiments, the tumor is a lung cancer, a cervical cancer, an epidermoid cancer, an ovarian cancer, a liver cancer, a bowel cancer, a stomach cancer or a pancreatic cancer.

In some embodiments, the tumor is a lung cancer, a liver cancer, a bowel cancer, a breast cancer or an esophageal cancer.

In a second aspect, the present disclosure provides a method of treating a tumor with multidrug resistance mediated by an ABC transporter in a subject in need thereof, comprising:

administering a combination of a peptide HX-12C shown in SEQ ID NO: 1 and an ABC transporter substrate chemotherapeutic drug to the subject.

In some embodiments, when the ABC transporter is the ABCB1, the tumor is a lung cancer, a cervical cancer, an epidermoid cancer, an ovarian cancer, a liver cancer, a bowel cancer, a stomach cancer or a pancreatic cancer.

In some embodiments, when the ABC transporter is the ABCC1, the tumor is a lung cancer, a liver cancer, a bowel cancer, a breast cancer or an esophageal cancer.

In some embodiments, when the ABC transporter is the ABCB1, the ABC transporter substrate chemotherapeutic drug is selected from the group consisting of a taxane, a vinca alkaloid, an anthracycline, an epipodophyllotoxin, a tyrosine kinase inhibitor and an antitumor antibiotic.

In some embodiments, when the ABC transporter is the ABCB1, the ABC transporter substrate chemotherapeutic drug is selected from the group consisting of paclitaxel, docetaxel, vinblastine, vincristine, adriamycin, daunorubicin, etoposide, teniposide, imatinib, nilotinib, erlotinib, dactinomycin D and a combination thereof.

In some embodiments, when the ABC transporter is the ABCC1, the ABC transporter substrate chemotherapeutic drug is selected from the group consisting of a vinca alkaloid, an anthracycline, an epipodophyllotoxin and a tyrosine kinase inhibitor.

In some embodiments, when the ABC transporter is the ABCC1, the ABC transporter substrate chemotherapeutic drug is selected from the group consisting of the anthracycline, the vinca alkaloid, the epipodophyllotoxin, camptothecin, methotrexate, saquinavir, mitoxantrone, imatinib and a combination thereof.

In a third aspect, the present disclosure provides a pharmaceutical composition for treating a tumor with multidrug resistance mediated by an ABC transporter, consisting of:

a peptide HX-12C shown in SEQ ID NO: 1 and an ABC transporter substrate chemotherapeutic drug.

In some embodiments, the ABC transporter is an ABCB1 transporter or an ABCC1 transporter.

In some embodiments, when the ABC transporter is the ABCB1 transporter, the ABC transporter substrate chemotherapeutic drug is selected from the group consisting of a taxane, a vinca alkaloid, an anthracycline, an epipodophyllotoxin, a tyrosine kinase inhibitor and an antitumor antibiotic.

In some embodiments, when the ABC transporter is the ABCB1 transporter, the ABC transporter substrate chemotherapeutic drug is selected from the group consisting of paclitaxel, docetaxel, vinblastine, vincristine, adriamycin, daunorubicin, etoposide, teniposide, imatinib, nilotinib, erlotinib, dactinomycin D and a combination thereof.

In some embodiments, when the ABC transporter is the ABCC1 transporter, the ABC transporter substrate chemotherapeutic drug is selected from the group consisting of a vinca alkaloid, an anthracycline, an epipodophyllotoxin and a tyrosine kinase inhibitor.

In some embodiments, when the ABC transporter is the ABCC1 transporter, the ABC transporter substrate chemotherapeutic drug is selected from the group consisting of the anthracycline, the vinca alkaloid, the epipodophyllotoxin, camptothecin, methotrexate, saquinavir, mitoxantrone, imatinib and a combination thereof.

The beneficial effects of the present disclosure are described as follows.

The peptide HX-12C provided herein can inhibit the function of the ABC transporter, and thus can increase the concentration of the chemotherapeutic drug in the drug-resistant tumor cells when administered in combination with the ABC transporter substrate chemotherapeutic drug, thereby inhibiting the proliferation of the drug-resistant tumor cells. The combination of the ABC transporter polypeptide inhibitor provided herein and the ABC transporter substrate chemotherapeutic drug has a promising application prospect in the treatment of tumors with multidrug resistance mediated by the ABC transporter.

The polypeptide provided herein plays a role in reversing the multidrug resistance of tumors mediated by the ABC transporter at a non-cytotoxic concentration by inhibiting the function of the ABC transporter, showing better safety and brilliant application prospect.

BRIEF DESCRIPTION OF THE DRAWINGS

FIG. 3A shows an expression of the ABCB1 protein after incubation with different concentrations of the peptide HX-12C for 72 h in KB-C2 cells; KB-3-1 cells without any treatment are used as a negative control of ABCB1 protein expression; GAPDH is used as a loading control; FIG. 3B shows a relative intensity of the expression of ABCB1 to the expression of GAPDH;

FIG. 4A shows an expression of the ABCC1 protein after incubation with different concentrations of the peptide HX-12C for 72 h in KB-CV60 cells; KB-3-1 cells without any treatment are used as a negative control of ABCB1 protein expression; GAPDH is used as a loading control; FIG. 4B shows a relative intensity of the expression of ABCB1 to the expression of GAPDH;

FIG. 7A shows an effect of the peptide HX-12C on the intracellular accumulation of [$^3$H]-paclitaxel in the KB-C2 and KB-3-1 cells; FIG. 7B shows an effect of the peptide HX-12C on the efflux of [$^3$H]-paclitaxel in the KB-C2 and KB-3-1 cells;

FIG. 8A shows an effect of the peptide HX-12C on the intracellular accumulation of [$^3$H]-vincristine in the KB-CV60 and KB-3-1 cells; FIG. 8B shows an effect of the peptide HX-12C on the efflux of [$^3$H]-vincristine in the KB-CV60 and KB-3-1 cells;

FIG. 10A schematically depicts domains and positions of the ABCB1 transporter binding with the peptide HX-12C; FIG. 10B schematically depicts a surface structure of a peptide HX-12C-ABCB1 complex; FIG. 10C schematically depicts a predicted binding mode of the peptide HX-12C with the ABCB1 transporter; FIG. 11A schematically depicts domains and positions of the ABCC1 transporter binding with the peptide HX-12C; and FIG. 11B schematically depicts a surface structure of a peptide HX-12C-ABCC1 complex.

DETAILED DESCRIPTION OF EMBODIMENTS

The disclosure will be further illustrated with reference to the accompanying drawings and embodiments. The experiments in the embodiments are all performed using conventional procedures unless otherwise specified. Materials, reagents and the like used in the following embodiments are commercially available unless otherwise specified. It should be understood that these embodiments are merely illustrative of the present disclosure, and are not intended to limit the scope of the present disclosure.

The polypeptides described below are synthesized by solid phase synthesis. Optionally, the synthesis can also be entrusted to a commercial company.

Example 1 Prediction and Analysis of a Secondary Structure of Peptide HX-12C

Figure 1A:
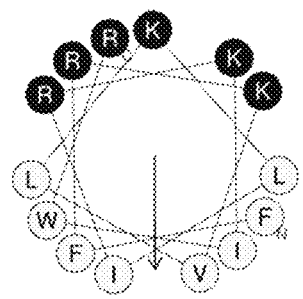
FIG. 1A schematically depicts a secondary structure of a peptide HX-12C.
Figure 1B:
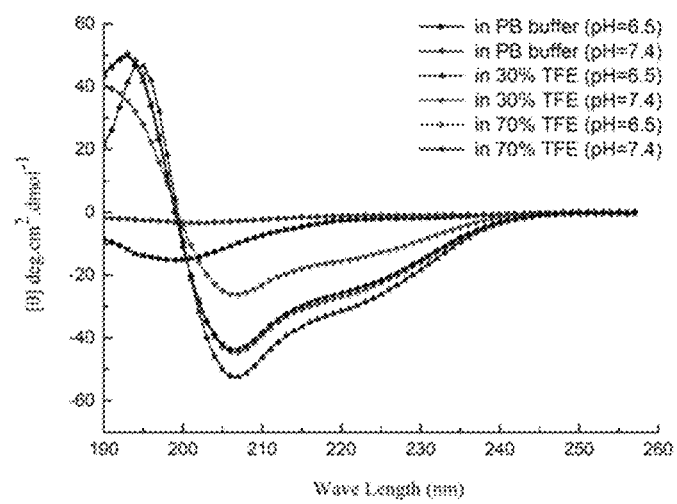
FIG. 1B is a circular dichroism analysis of the secondary structure of the peptide HX-12C.

A secondary structure of an antimicrobial peptide HX-12C was predicted through secondary structure prediction service, and was analyzed through circular dichroism. As shown in FIG. 1, the predicted secondary structure of the peptide HX-12C showed a typical characteristic of an amphiphilic molecular that a hydrophobic surface and a hydrophilic of the peptide HX-12C were regularly distributed on both sides of the peptide helix. The prediction was verified by the circular dichroism analysis, in which the circular dichroism spectrum of the peptide HX-12C in aqueous phases (0.01 mol/L phosphate buffer) showed the peptide HX-12C had an irregular secondary structure, and the circular dichroism spectrum of the peptide HX-12C in membrane phases (30% trifluoroethanol (TFE) solution or 70% TEF solution) showed the peptide HX-12C had a typical α-helix secondary structure. An acidic environment was more conducive to a formation of the helix structure, which further explained an interaction between the peptide HX-12C and the cell membrane, especially for tumor cells.

Example 2 Effect of Peptide HX-12C on ABCB1-Overexpressing Cell Lines

Figure 2A:
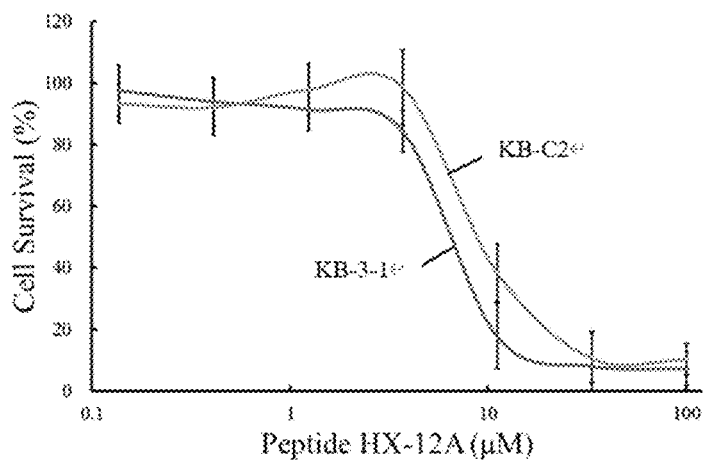
FIGS. 2A-2C show survival curves of a drug-selected ABCB1-overexpressing cell line (KB-C2) and its parental cell line (KB-3-1) versus concentration of a peptide, where 2A: peptide HX-12A; 2B: peptide HX-12B; and 2C: peptide HX-12C.
Figure 2B:
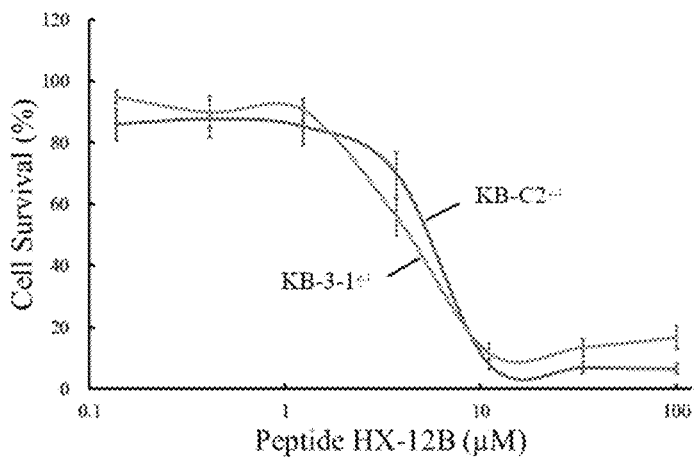
Figure 2C:
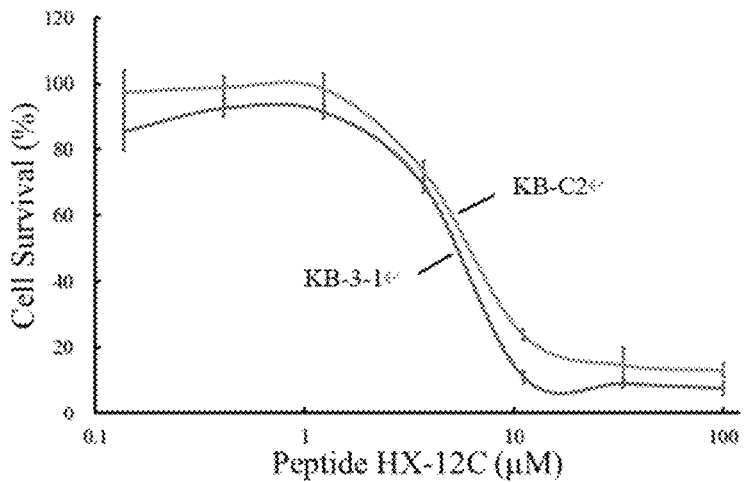

In order to determine an effect of the peptide HX-12C on the ABC transporter, a sensitivity of an ABCB1-overexpressing cell KB-C2 to the peptide HX-12C was tested. Cytotoxicity of the peptide HX-12C in different cell lines was determined by MTT ((3-[4,5-dimethylthiazol-2-yl]-2,5 diphenyl tetrazolium bromide) assay, in which 5000 cells/well were seeded in a 96-well microplate and incubated overnight. The cells were then added with the peptide HX-12C with a designated concentration gradient, and incubated for 68 h. Each well was added with 20 μL of a MTT solution (4 mg/mL), and incubated for another 4 h. After aspirating the culture medium, a formaldehyde crystal was dissolved using 100 μL of dimethyl sulfoxide (DMSO). An absorbance was determined at 570 nm using an ultraviolet-visible spectrophotometer. As shown in FIG. 2, half maximal inhibitory concentrations $IC_{50}$ values of peptides HX-12A (FFRKVLKLIRKI, as shown in SEQ ID NO: 2), HX-12B (FFRKVLKLIRKIF, as shown in SEQ ID NO: 3) and HX-12C in ABCB1-overexpressing cancer cells (KB-C2) were 6.45 μM, 7.61 μM, and 6.06 μM, respectively. The $IC_{50}$ values of these peptides in parental cells (KB-3-1) were 9.18 μM, 5.42 μM, and 7.53 μM, respectively (FIG. 2). These peptides would not produce significant cytotoxicity at a concentration lower than 3 μM, and were selected for the reversal study.

Example 3 Effect of Peptide HX-12C on ABCC1-Overexpressing Cell Line

In order to determine an effect of the peptide HX-12C on the ABC transporter, a sensitivity of an ABCC1-overexpressing cell KB-CV60 to the peptide HX-12C was tested. Cytotoxicity of the peptide HX-12C in different cell lines was determined by MTT ((3-[4,5-dimethylthiazol-2-yl]-2,5 diphenyl tetrazolium bromide) assay, in which 5000 cells/well were seeded in a 96-well microplate and incubated overnight. The cells were then added with the peptide HX-12C with a designated concentration gradient, and incubated for 68 h. Each well was added with 20 μL of a MTT solution (4 mg/mL), and incubated for another 4 h. After aspirating the culture medium, a formaldehyde crystal was dissolved using 100 μL of dimethyl sulfoxide (DMSO). An absorbance was determined at 570 nm using an ultraviolet-visible spectrophotometer. As shown in Table. 1, half maximal inhibitory concentrations $IC_{50}$ values of peptides HX-12A (FFRKVLKLIRKI, as shown in SEQ ID NO: 2), HX-12B (FFRKVLKLIRKIF, as shown in SEQ ID NO: 3) and HX-12C in ABCC1-overexpressing cancer cells (KB-C2) were 24.95 μM, 7.41 μM, and 6.38 μM, respectively. The $IC_{50}$ values of these peptides in parental cells KB-CV60 were 20.55 mM, 5.16 μM, and 6.26 μM, respectively. These peptides would not produce significant cytotoxicity at a concentration lower than 3 μM, and were selected for the reversal study.

TABLE 1

Cytotoxicity of peptides

| Treatment | $IC_{50}$ (RM) | |
| --- | --- | --- |
|  | KB-3-1 | KB-CV60 |
| HX-12A | 20.55 | 24.95 |
| HX-12B | 5.16 | 7.41 |
| HX-12C | 6.26 | 6.38 |
| Vincristine | 0.095 | 16.06 |
| Cisplatin | 2.29 | 2.96 |

Example 4 Investigation on Reversal Effect of Peptide HX-12C on Drug Resistance of ABCB1-Overexpressing Cell Line To determine whether the peptide HX-12C can reverse multi-drug resistance (MDR) mediated by ABCB1 transporter, the sensitivity of drug-induced resistant tumor cell line (KB-C2), the transfected ABCB1-overexpressing cell lines (HEK293/ABCB1) (Shi Z, Tiwari A K, Shukla S, et al. Sildenafil Reverses ABCB1- and ABCG2-Mediated Chemotherapeutic Drug Resistance[J]. Cancer Research, 2011, 71(8):3029-3041.) and their parental cell lines (KB-3-1 and HEK293/pcDNA3.1) to the peptide HX-12C were tested. The test results were shown in Tables. 2-3. Compared to the parental cell lines (KB-3-1 and HEK293/pcDNA3.1), the peptide HX-12C reduced the $IC_{50}$ values of ABCB1 overexpressing cell lines (KB-C2 and HEK293/ABCB1) to paclitaxel and doxorubicin. In addition, compared to the corresponding parental cell lines (KB-3-1 and HEK293/pc DNA3.1), the peptide HX-12C did not change $IC_{50}$ values of cisplatin (a non-substrate of ABCB1) in ABCB1-overexpressing cell lines (KB-C2 and HEK293/ABCB1) (Table. 4). These results showed that the peptide HX-12C can reverse the MDR of cancer cells mediated by ABCB1 overexpression, whereas the peptide HX-12A and the peptide HX-12B had no reversal effect under the same condition, although the peptide HX-12A and the peptide HX-12B only had 1 to 2 amino acids different with the peptide HX-12C.

TABLE 2

Reversal effects of peptides on drug-induced ABCB1-overexpressing cancer cell lines

| Treatment | $IC50^1$ (μm) ($RF^2$) | |
| --- | --- | --- |
| | KB-3-1 | KB-C2 |
| Paclitaxel | 0.002 ± 0.0007 (1.00) | 1.430 ± 0.241 (715.00) |
| + HX-12A (3 μM) | 0.005 ± 0.0004 (2.50) | 1.389 ± 0.356 (694.50) |
| + HX-12B (3 μM) | 0.001 ± 0.0006 (1.50) | 0.542 ± 0.097 (271.00) |
| + HX-12C (3 μM) | 0.003 ± 0.0007 (1.50) | 0.031 ± 0.002*** (15.50) |
| + Verapamil (3 μM) | 0.001 ± 0.0002 (0.50) | 0.030 ± 0.004*** (15.00) |
| Doxorubicin | 1.186 ± 0.279 (1.00) | 69.79 ± 4.637 (58.84) |
| + HX-12A (3 μM) | 1.099 ± 0.169 (0.93) | 65.41 ± 0.281 (55.15) |
| + HX-12B (3 μM) | 1.042 ± 0.211 (0.88) | 40.21 ± 0.206 (33.90) |
| + HX-12C (3 μM) | 1.012 ± 0.060 (0.85) | 1.454 ± 0.015*** (1.23) |
| + Verapamil (3 μM) | 0.897 ± 0.143 (0.76) | 0.734 ± 0.165*** (0.62) |
| Cisplatin | 1.793 ± 0.476 (1.00) | 2.025 ± 0.428 (1.13) |
| + HX-12A (3 μM) | 1.687 ± 0.398 (0.94) | 2.503 ± 0.336 (1.40) |
| + HX-12B (3 μM) | 1.593 ± 0.512 (0.89) | 2.096 ± 0.389 (1.17) |
| + HX-12C (3 μM) | 1.693 ± 0.452 (0.94) | 2.087 ± 0.233 (1.16) |
| + Verapamil (3 μM) | 1.676 ± 0.478 (0.93) | 2.107 ± 0.361 (1.18) |

TABLE 3

Reversal effects of peptides on transfected ABCB1-overexpressing cancer cell lines

| Treatment | $IC50^1$ (μm) ($RF^2$) | |
| --- | --- | --- |
| | HEK293/pcDNA3.1 | HEK293/ABCB1 |
| Paclitaxel | 1.449 ± 0.121 (1.00) | 30.924 ± 4.665 (21.34) |
| + HX-12A (3 μM) | 1.405 ± 0.285 (0.97) | 22.117 ± 1.199 (15.26) |
| + HX-12B (3 μM) | 1.302 ± 0.255 (0.90) | 20.190 ± 1.047 (13.93) |
| + HX-12C (3 μM) | 1.446 ± 0.462 (1.00) | 1.501 ± 0.342*** (1.04) |
| + Verapamil (3 μM) | 1.486 ± 0.377 (1.03) | 1.708 ± 0.147*** (1.18) |
| Doxorubicin | 1.235 ± 0.571 (1.01) | 31.233 ± 5.406 (25.29) |
| + HX-12A (3 μM) | 1.206 ± 0.405 (0.98) | 25.327 ± 4.318 (20.51) |
| + HX-12B (3 μM) | 1.221 ± 0.488 (0.99) | 22.374 ± 3.774 (18.12) |
| + HX-12C (3 μM) | 1.420 ± 0.453 (1.15) | 1.182 ± 0.253*** (0.96) |
| + Verapamil (3 μM) | 1.271 ± 0.358 (1.03) | 1.245 ± 0.265*** (1.00) |
| Cisplatin | 2.214 ± 0.541 (1.00) | 2.665 ± 0.208 (1.20) |
| + HX-12A (3 μM) | 2.337 ± 0.438 (1.06) | 2.525 ± 0.284 (1.14) |
| + HX-12B (3 μM) | 2.403 ± 0.389 (1.09) | 2.692 ± 0.176 (1.22) |
| + HX-12C (3 μM) | 2.464 ± 0.144 (1.11) | 2.184 ± 0.317 (0.99) |
| + Verapamil (3 μM) | 2.128 ± 0.238 (0.96) | 2.287 ± 0.138 (1.03) |

Example 5 Investigation on Reversal Effect of Peptide HX-12C on Drug Resistance of ABCC1-Overexpressing Cell Line To determine whether the peptide HX-12C can reverse multi-drug resistance (MDR) mediated by ABCC1 transporter, the sensitivity of drug-induced resistant tumor cell line (KB-CV60), the transfected ABCC1-overexpressing cell lines (HEK293/ABCC1) (Shi Z, Tiwari A K, Shukla S, et al. Sildenafil Reverses ABCB1- and ABCG2-Mediated Chemotherapeutic Drug Resistance[J]. Cancer Research, 2011, 71(8):3029-3041.) and their parental cell lines (KB-3-1 and HEK293/pcDNA3.1) to the peptide HX-12C were tested. The test results were shown in Tables. 4-5. Compared to the parental cell lines (KB-3-1 and HEK293/pcDNA3.1), the peptide HX-12C reduced the $IC_{50}$ values of ABCB1 overexpressing cell lines (KB-CV60 and HEK293/ABCC1) to vincristine. In addition, compared to the corresponding parental cell lines (KB-3-1 and HEK293/pc DNA3.1), the peptide HX-12C did not change $IC_{50}$ values of cisplatin (a non-substrate of ABCC1) in ABCC1-overexpressing cell lines (KB-CV60 and HEK293/ABCC1)(Table. 4). These results showed that the peptide HX-12C can reverse the MDR of cancer cells mediated by ABCC1 overexpression.

TABLE 4

Reversal effects of peptides on drug-induced ABCC1-overexpressing cancer cell lines

| Treatment | $IC50$ (μm) ($RF^1$) | |
| --- | --- | --- |
| | KB-3-1 | KB-CV60 |
| Vincristine | 0.095 (1.00) | 16.06(169.05) |
| + HX-12C (3 μM) | 0.168 (1.77) | 0.254***(2.67) |
| + MK571 (5 μM) | 0.164 (1.73) | 0.232***(2.27) |
| Cisplatin | 1.793 (1.00) | 2.233(1.25) |
| + HX-12C (3 μM) | 1.693 (0.94) | 1.942(1.08) |
| + MK571(5 μM) | 1.496 (0.83) | 1.7250.96) |

TABLE 5

Reversal effects of peptides on transfected ABCC1-overexpressing cancer cell lines

| Treatment | $IC_{50}$ (μm) ($RF^1$) | |
| --- | --- | --- |
| | HEK293/pcDNA3.1 | HEK293/ABCC1 |
| Vincristine | 0.137 (1.00) | 2.710(19.79) |
| + HX-12C(3 μM) | 0.143 (1.04) | 0.149***(1.09) |
| + MK571 (5 μM) | 0.140 (1.02) | 0.138***(1.01) |
| Cisplatin | 2.214 (1.00) | 2.235(1.01) |
| + HX-12C (3 μM) | 2.464 (1.11) | 2.176(0.98) |
| + MK571(5 μM) | 2.201 (0.99) | 2.456(1.11) |

Example 6 Effect of Peptide HX-12C on Expression of ABCB1 Transporter

Figure 3A:
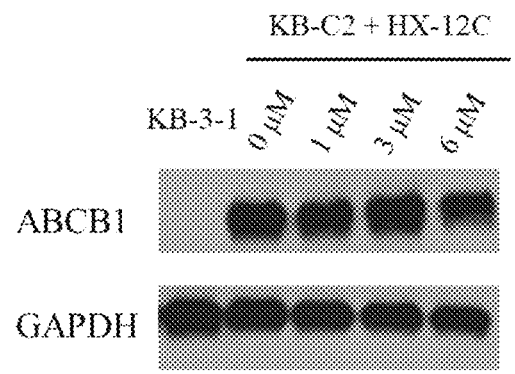
FIGS. 3A-3B show an expression of ABCB1 in the ABCB1-overexpressing cell line detected by Western blotting method.
Figure 3B:
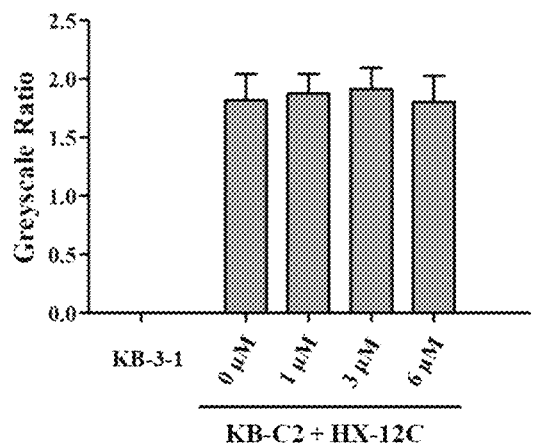

Western blotting analysis was performed to determine whether the peptide HX-12C affected the expression of ABCB1 transporter. The KB-C2 and non-treated KB-3-1 cells were treated with 0, 1, 3 and 6 μM of the peptide HX-12C for 72 h, and then incubated with a lysis buffer (containing 2.5% 1M Tris, 0.15% EDTA, 1% sodium deoxycholate, 0.1% sodium dodecyl sulfate (SDS), 0.88% NaCl, 1% Triton-X and a protease inhibitor) on ice for 20 min, and centrifuged at 4° C. to collect a supernatant. A protein concentration of the supernatant was determined by bicinchoninic acid (BCA)-based protein assay. Each protein sample was loaded and separated by SDS-polyacrylamide gel electrophoresis. After that, the gel was transferred to a polyvinylidene fluoride (PVDF) membrane followed by blocking with 5% milk for 2 h. The PVDF membrane was then incubated with a primary antibody (1:1000 dilution for both anti-P-glycoprotein and anti-GAPDH antibodies) at 4° C. overnight. Then the PVDF membrane was washed with TBST (Tris buffer, 0.1% Tween 20) buffer, and incubated with secondary horseradish peroxidase (HRP)-labeled antibodies ((1:1000 dilution for an anti-mouse antibody). The signal was detected by enhanced chemiluminescence, and the protein expression was quantified by a software. As shown in FIGS. 3A and 3B, different concentrations (0, 1, 3, 6 µM) of the peptide HX-12C treatment had no significant effect on the expression of ABCB1 protein (172 kDa) in the over-expressing KB-C2 cell lines.

Example 7 Effect of Peptide HX-12C on Expression of ABCC1 Transporter

Figure 4A:
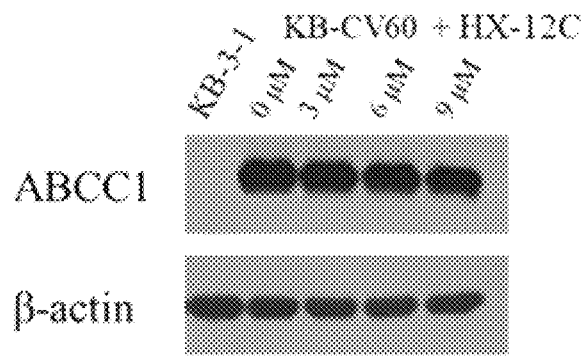
FIGS. 4A-4B show an expression of ABCC1 in the ABCC1-overexpressing cell line detected by Western blotting method.
Figure 4B:
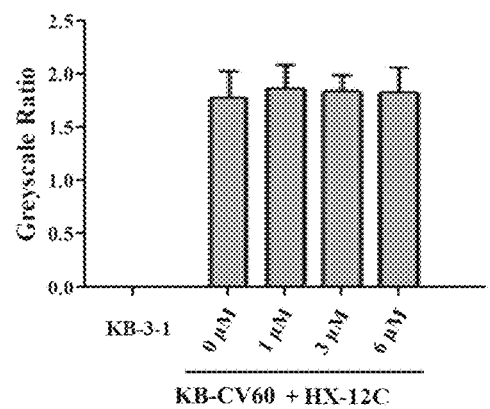

Western blotting analysis was performed to determine whether the peptide HX-12C affected the expression of ABCC1 transporter. The KB-C2 and non-treated KB-CV60 cells were treated with 0, 1, 3 and 6 µM of the peptide HX-12C for 72 h, and then incubated with a lysis buffer (containing 2.5% 1M Tris, 0.15% EDTA, 1% sodium deoxycholate, 0.1% sodium dodecyl sulfate (SDS), 0.88% NaCl, 1% Triton-X and a protease inhibitor) on ice for 20 min, and centrifuged at 4° C. to collect a supernatant. A protein concentration of the supernatant was determined by bicinchoninic acid (BCA)-based protein assay. Each protein sample was loaded and separated by SDS-polyacrylamide gel electrophoresis. After that, the gel was transferred to a polyvinylidene fluoride (PVDF) membrane followed by blocking with 5% milk for 2 h. The PVDF membrane was then incubated with a primary antibody (1:1000 dilution for both anti-P-glycoprotein and anti-GAPDH antibodies) at 4° C. overnight. Then the PVDF membrane was washed with TBST (Tris buffer, 0.1% Tween 20) buffer, and incubated with secondary horseradish peroxidase (HRP)-labeled antibodies ((1:1000 dilution for an anti-mouse antibody). The signal was detected by enhanced chemiluminescence, and the protein expression was quantified by a software. As shown in FIGS. 4A and 4B, different concentrations (0, 1, 3, 6 µM) of the peptide HX-12C treatment had no significant effect on the expression of ABCC1 protein (190 kDa) in the over-expressing KB-CV60 cell lines.

Example 8 Effect of Peptide HX-12C on Expression Level and Cell Localization OF ABCB1

Figure 5:
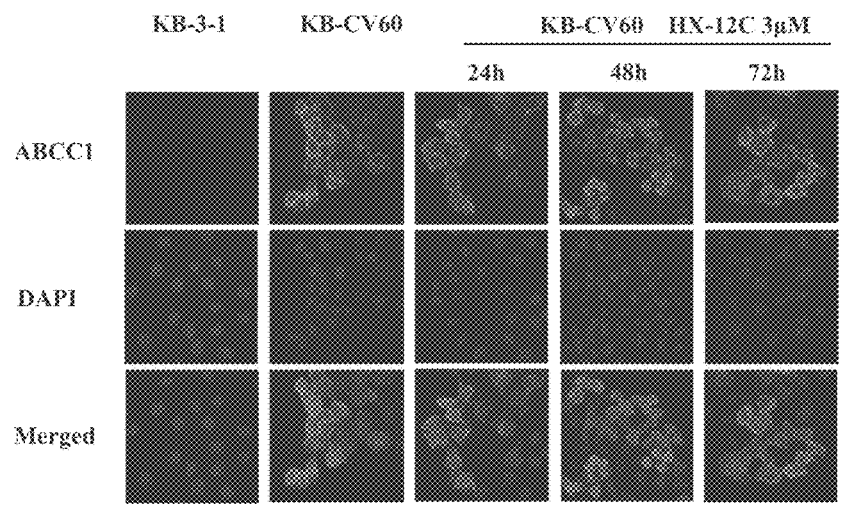
FIG. 5 shows an expression and cellular localization of ABCB1 protein in the KB-3-1 and KB-C2 cells after incubation with the peptide HX-12C.

In order to further confirm whether the peptide HX-12C affected the expression and cell localization of the ABCB1 protein, immunofluorescence staining was performed after treating the cells after different incubation times of the peptide HX-12C. The KB-3-1 and KB-C2 cells were seeded in 24-well plates ($1 \times 10^4$ cells/well), and incubated at 37° C. for 24 h. The cells were then incubated with 3 µM of the peptide HX-12C for 0, 24, 48 and 72 h, respectively, washed twice with a cold phosphate buffer saline (PBS) solution, fixed in 4% formaldehyde for 15 min and permeablized with 0.25% Triton X-100 for 15 min. After being incubated with BSA (6% in PBS) for 1 h, the cells were incubated with monoclonal anti-Pglycoprotein Clone F4 primary antibody with a dilution of 1:1000 at 4° C. overnight, and then further incubated with Alexa Fluor 488 conjugated rabbit anti-mouse IgG secondary antibody with dilution of 1:1000 for 1 h in the dark. The nuclei were counterstained with 4',6-diamidino-2-phenylindole (DAPI) and observed with a fluorescence microscope. As shown in FIG. 5, compared to the parental cells KB-3-1, the ABCB1 protein was significantly expressed on the membrane of KB-C2 cells. The fluorescent intensity of ABCB1 protein in KB-C2 remained unchanged after the treatment of peptide HX-12C, which was consistent with the result of Western blot analysis. In addition, the peptide HX-12C had no significant effect on the subcellular distribution pattern of ABCB1 protein on the membrane of KB-C2 cells. These results showed that the reversal of MDR by the peptide HX-12C was not caused by decreasing the protein expression or change the protein location.

Example 9 Effect of Peptide HX-12C on Expression Level and Cellular Localization ABCC1

Figure 6:
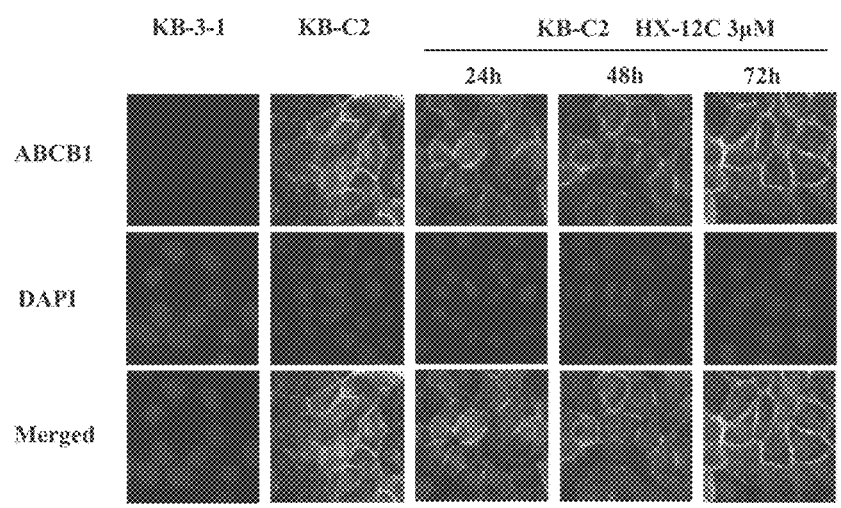
FIG. 6 shows an expression and cellular localization of ABCC1 protein in the KB-3-1 and KB-CV60 cells after incubation with the peptide HX-12C.

In order to further confirm whether the peptide HX-12C affected the expression and cell localization of the ABCC1 protein, immunofluorescence staining was performed after treating the cells after different incubation times of the peptide HX-12C. The KB-CV60 and KB-C2 cells were seeded in 24-well plates ($1 \times 10^4$ cells/well), and incubated at 37° C. for 24 h. The cells were then incubated with 3 µM of the peptide HX-12C for 0, 24, 48 and 72 h, respectively, washed twice with a cold phosphate buffer saline (PBS) solution, fixed in 4% formaldehyde for 15 min and permeablized with 0.25% Triton X-100 for 15 min. After being incubated with BSA (6% in PBS) for 1 h, the cells were incubated with monoclonal anti-Pglycoprotein Clone F4 primary antibody with a dilution of 1:1000 at 4° C. overnight, and then further incubated with Alexa Fluor 488 conjugated rabbit anti-mouse IgG secondary antibody with dilution of 1:1000 for 1 h in the dark. The nuclei were counterstained with 4',6-diamidino-2-phenylindole (DAPI) and observed with a fluorescence microscope. As shown in FIG. 6, compared to the parental cells KB-3-1, the ABCC1 protein was significantly expressed on the membrane of KB-C2 cells. The fluorescent intensity of ABCC1 protein in KB-CV60 remained unchanged after the treatment of peptide HX-12C, which was consistent with the result of Western blot analysis. In addition, the peptide HX-12C had no significant effect on the subcellular distribution pattern of ABCC1 protein on the membrane of KB-CV60 cells. These results showed that the reversal of MDR by the peptide HX-12C was not caused by decreasing the protein expression or change the protein location.

Figure 7A:
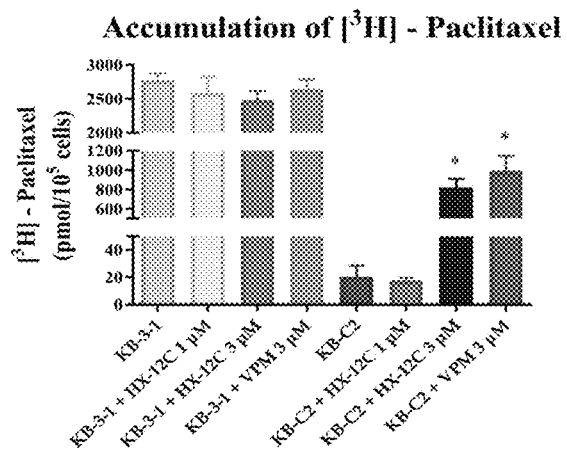
FIGS. 7A-7B show an effect of the peptide HX-12C on intracellular accumulation and efflux of [$^3$H]-paclitaxel in the KB-C2 and KB-3-1 cells.
Figure 7B:
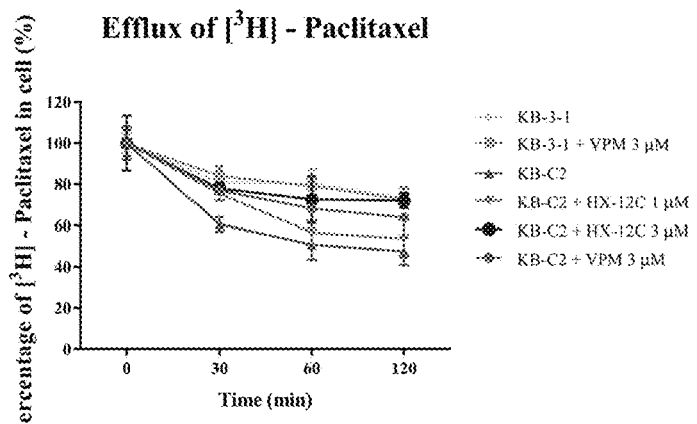

Example 10 Effect of Peptide HX-12C on Accumulation and Efflux of [$^3$H]-Paclitaxel The effect of the peptide HX-12C on accumulation and efflux of [$^3$H]-paclitaxel in the ABCB1-overexpressing cells was determined by comparing the concentrations of [$^3$H]-paclitaxel in the KB-3-1 cells and the KB-C2 cells. The KB-3-1 and KB-C2 cells were seeded in a 24-well plate ($1 \times 10^4$ cells/well) and incubated at 37° C. for 24 h. The cells were incubated for 72 h in the presence or absence of the peptide HX-12C and the positive reversal agent verapamil, and the medium was then replaced by a medium containing 5 µM of [$^3$H]-paclitaxel and the peptide HX-12C or the positive reversal agent. After a 2-hour incubation, the medium was removed, and the cells were washed with ice-cold PBS three times and transferred to a scintillation fluid after lysis. A drug efflux analysis was performed, the operation was similar to the cumulative analysis. After discarding the medium containing [$^3$H]-paclitaxel, the cells were washed with ice-cold PBS and incubated with a medium containing the peptide HX-12C or the positive reversal agent. Samples were taken at 30, 60, and 120 minutes. The cells were washed three times followed by lysis, and then transferred to the scintillation fluid. The radioactivity was measured with a liquid scintillation analyzer. The results were shown in FIG. 7A. After the 2-h incubation, the intracellular [$^3$H]-paclitaxel in in ABCB1-overexpressing cells KB-C2 was about 100 times that of the parent cells KB-3-1. Compared with the control group, the intracellular concentration of [$^3$H]-paclitaxel in the KB-C2 cells was significantly increased with the peptide HX-12C (3 µM) treatment, and the effect of the peptide HX-12C (3 µM) on the accumulation of [$^3$H]-paclitaxel was comparable to that of the ABCB1 inhibitor verapamil (3 In addition, the effect of peptide HX-12C on the efflux of [$^3$H]-paclitaxel in ABCB1-overexpressing KB-C2 cells was evaluated, and the results were shown in FIG. 7B. After the 2-hour incubation, the intracellular [$^3$H]-paclitaxel level in KB-3-1 cells did not change significantly, and the inhibitor verapamil did not change the efflux function of KB-3-1 cells. However, the level of intracellular [$^3$H]-paclitaxel in KB-C2 cells without inhibitor treatment was significantly decreased by about 50%. It was demonstrated that the peptide HX-12C (3 µM) can effectively inhibit the efflux function of KB-C2 cells.

Figure 8A:
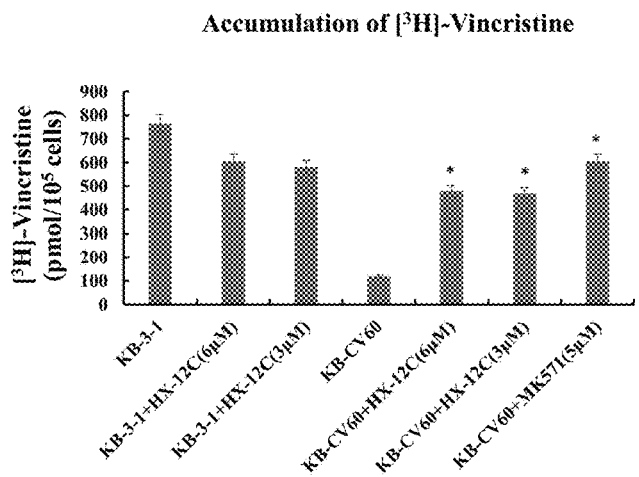
FIGS. 8A-8B show an effect of the peptide HX-12C on intracellular accumulation and efflux of [$^3$H]-vincristine in the KB-CV60 and KB-3-1 cells.
Figure 8B:
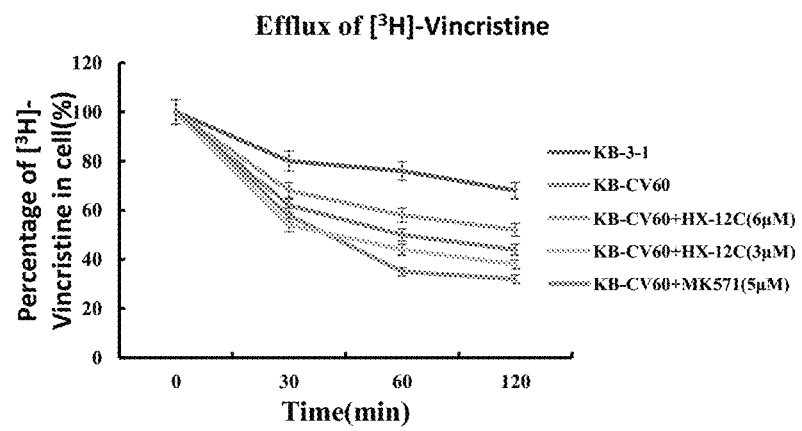

Example 11 Effect of Peptide HX-12C on the Accumulation and Efflux of [$^3$H]-Vincristine The effect of the peptide HX-12C on accumulation and efflux of [$^3$H]-vincristine in the ABCC1-overexpressing cells was determined by comparing the concentrations of [$^3$H]-vincristine in the KB-3-1 cells and the KB-CV60 cells. The KB-3-1 and KB-CV60 cells were seeded in a 24-well plate (1×10$^4$ cells/well) and incubated at 37° C. for 24 h. The cells were incubated for 72 h in the presence or absence of the peptide HX-12C and the positive reversal agent MK571, and the medium was then replaced by a medium containing 5 µM of [$^3$H]-vincristine and the peptide HX-12C or the positive reversal agent. After a 2-hour incubation, the medium was removed, and the cells were washed with ice-cold PBS three times and transferred to a scintillation fluid after lysis. A drug efflux analysis was performed, the operation was similar to the cumulative analysis. After discarding the medium containing [$^3$H]-vincristine, the cells were washed with ice-cold PBS and incubated with a medium containing the peptide HX-12C or the positive reversal agent. Samples were taken at 30, 60, and 120 minutes. The cells were washed three times followed by lysis, and then transferred to the scintillation fluid. The radioactivity was measured with a liquid scintillation analyzer. The results were shown in FIG. 8A. After the 2-h incubation, the intracellular [$^3$H]-vincristine in in ABCC1-overexpressing cells KB-CV60 was about seven times that of the parent cells KB-3-1. Compared with the control group, the intracellular concentration of [$^3$H]-vincristine in the KB-CV60 cells was significantly increased with the peptide HX-12C (3 µM) treatment, and the effect of the peptide HX-12C (3 µM) on the accumulation of [$^3$H]-vincristine was comparable to that of the ABCC1 inhibitor MK571 (5 In addition, the effect of peptide HX-12C on the efflux of [$^3$H]-vincristine in ABCC1-overexpressing KB-CV60 cells was evaluated, and the results were shown in FIG. 8B. After the 2-hour incubation, the intracellular [$^3$H]-vincristine level in KB-3-1 cells decreased by 25%, and the intracellular [$^3$H]-vincristine level in KB-CV60 cells without inhibitor treatment was significantly decreased by about 70%. The intracellular [$^3$H]-vincristine level in KB-CV60 cells treated with the peptide HX-12C (3 µM) decreased by 58%, which was equivalent to the effect of the inhibitor MK571. It was demonstrated that the peptide HX-12C (3 µM) can effectively inhibit the efflux function of KB-CV60 cells.

Example 12 Effect of Peptide HX-12C on ABCB1 Transporter ATPase Activity

Figure 9:
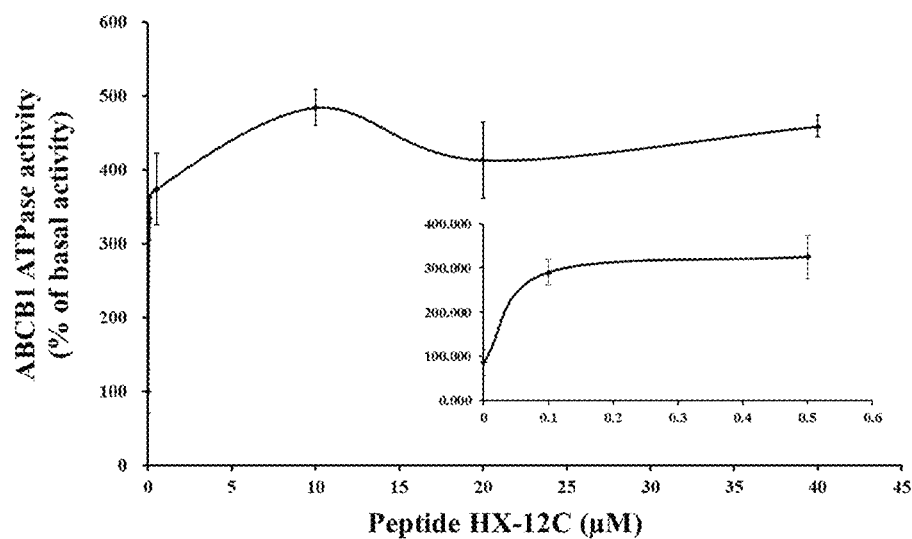
FIG. 9 shows effect of peptide HX-12C on an ATPase activity of the ABCB1 transporter.

The hydrolysis of ATP mediated by ABCB1 in the presence of different concentrations (0-40 µM) of the peptide HX-12C was measured to evaluate the effect of peptide HX-12C on ABCB1 ATPase activity. Membrane vesicles (10 µg of protein) were incubated in ATPase buffer at 37° C. for 5 min with or without 0.3 mM of vanadate, and then added with the peptide HX-12C at a concentration of 0 to 40 µM and the buffer and incubated at 37° C. for 3 min. After adding 5 mM of Mg-ATP with a total volume of 0.1 mL, an ATPase reaction was initiated until stopped by adding 100 µL of 5% SDS solution after incubation at 37° C. for 20 min. The ATPase activity of ABCB1 was calculated according to the amount of released inorganic phosphorus (IP) detected at 800 nm using a spectrophotometer. The results were shown in FIG. 9. The peptide HX-12C stimulated the ATPase activity of ABCB1 in a concentration-dependent manner, and the maximum stimulation amount is 4.7 times the basic activity. The concentration of peptide HX-12C required for 50% stimulation of ATPase activity of ABCB1 was 0.65 µM, which was much lower than the cytotoxic concentration. These results showed that the peptide HX-12C may interact with drug-substrate binding sites and affect the ATPase activity of ABCB1.

Example 13 Analysis of Peptide HX-12C-ABCB1 Binding by Molecular Docking

Figure 10A:
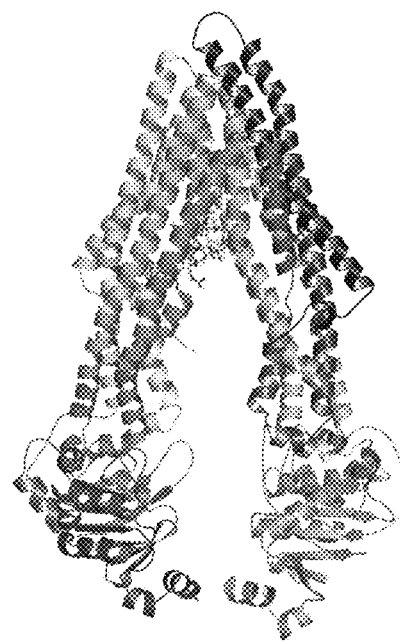
FIGS. 10A-10C schematically depict a molecular binding between the peptide HX-12C and the ABCB1 transporter.
Figure 10B:
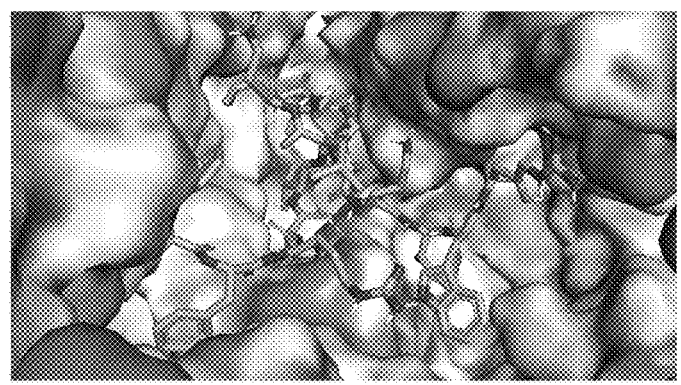
Figure 10C:
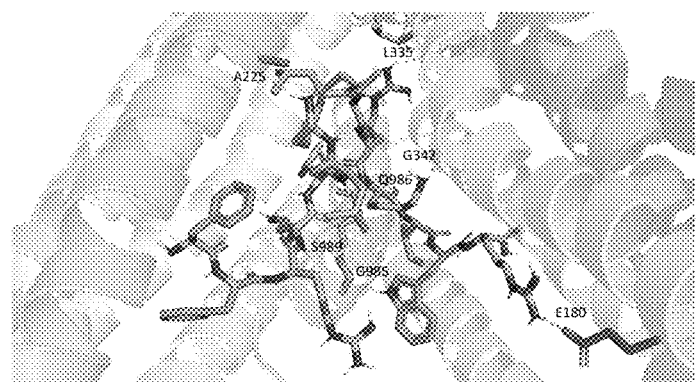

Molecular docking was performed to obtain a potential binding mode and rationalize the observation effect of the peptide HX-12C. The peptide HX-12C was depicted using Sybyl/Sketch module (Tripos Inc., USA), and optimized by the Powell method. The convergence parameter was set at 0.05 kcal/(Amol), and assigned by the Gasteiger-Hsckel method. The crystal structure of ABCB1 was obtained from the RCSB Protein Data Bank protein database (PDB-ID: 4M2T). The peptide HX-12C was docked into the active site of ABCB1. Tripos force field and Pullman charge was used to remove the ligand, and add hydrogen and minimize the hydrogen. Other docking parameters remained default values. The results were shown in FIG. 10. The peptide HX-12C tightly bonded to the active site (substrate binding site) of ABCB1. The peptide HX-12C formed eight hydrogen bonds with residues E180, A225, L335, G342, G985, Q986 and S989 in ABCB1, which may improve the binding affinity of the peptide HX-12C to ABCB1. It should be noted that the salt bridge containing arginine in the peptide HX-12C and E180 in ABCB1 may help to improve the binding affinity. In addition, the peptide HX-12C was in hydrophobic contact with residues such as F299, F990, L232 and I302 in ABCB1.

Example 14 Analysis of Peptide HX-12C-ABCC1 Binding by Molecular Docking

Figure 11A:
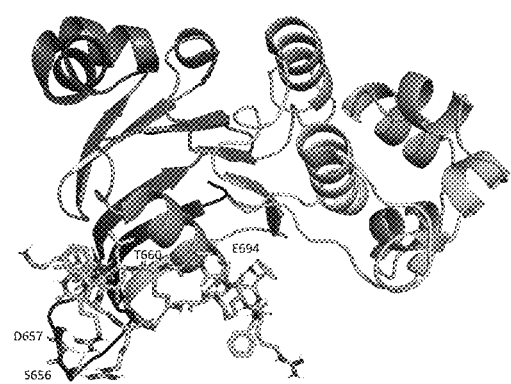
FIGS. 11A-11B schematically depict a molecular binding between the peptide HX-12C and the ABCC1 transporter.
Figure 11B:
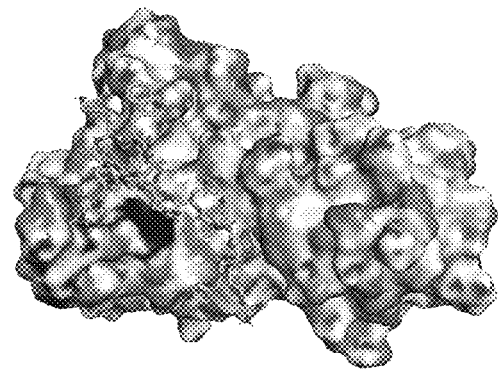

Molecular docking was performed to obtain a potential binding mode and rationalize the observation effect of the peptide HX-12C. The peptide HX-12C was depicted using Sybyl/Sketch module (Tripos Inc., USA), and optimized by the Powell method. The convergence parameter was set at 0.05 kcal/(Amol), and assigned by the Gasteiger-Hsckel method. The crystal structure of ABCC1 was obtained from the RCSB Protein Data Bank protein database (PDB-ID: 4M2T). The peptide HX-12C was docked into the active site of ABCC1. Tripos force field and Pullman charge was used to remove the ligand, and add hydrogen and minimize the hydrogen. Other docking parameters remained default values. The results were shown in FIG. 11. The peptide HX-12C bonded tightly to the nucleotide-binding domains (NBD) region of ABCC1. The peptide HX-12C can form hydrogen bonds with QS656, D657, T660 and E694. Phenylalanine in the structure was also an important part for maintaining the binding force that the phenylalanine hydrophobically interacted with the surrounding Y710, P712 and W716, and formed π-π stacking due to an overlap with the pyrrole ring in W716. In addition, the arginine can form a hydrogen bond with D657 and a salt bridge, greatly enhancing the binding affinity.

What is claimed is:

1. A method of treating a tumor with multidrug resistance mediated by an ABC transporter in a subject in need thereof, comprising:
    administering a combination of 3 μM of a peptide HX-12C shown in SEQ ID NO: 1 and an ABC transporter substrate chemotherapeutic drug to the subject;
    wherein the ABC transporter is ABCC1.

2. The method of claim 1, wherein the ABC transporter substrate chemotherapeutic drug is selected from the group consisting of vinca alkaloids, anthracyclines, epipodophyllotoxins and tyrosine kinase inhibitors.

3. The method of claim 2, wherein the ABC transporter substrate chemotherapeutic drug is selected from the group consisting of anthracyclines, vinca alkaloids, epipodophyllotoxins, camptothecin, methotrexate, saquinavir, mitoxantrone, imatinib and a combination thereof.

4. A pharmaceutical composition for treating a tumor with multidrug resistance mediated by an ABC transporter, consisting of:
    3 μM of a peptide HX-12C shown in SEQ ID NO: 1; and
    an ABC transporter substrate chemotherapeutic drug;
    wherein the ABC transporter is ABCC1, and the ABC transporter substrate chemotherapeutic drug is selected from the group consisting of a vinca alkaloid, an anthracycline, an epipodophyllotoxin and tyrosine kinase inhibitor.

5. The pharmaceutical composition of claim 4, wherein the ABC transporter substrate chemotherapeutic drug is selected from the group consisting of the anthracycline, the vinca alkaloid, the epipodophyllotoxin, camptothecin, methotrexate, saquinavir, mitoxantrone, imatinib and a combination thereof.

* * * * *

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: synthetic

<400> SEQUENCE: 1

Phe Phe Arg Lys Val Leu Lys Leu Ile Arg Lys Ile Trp Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Phe Phe Arg Lys Val Leu Lys Leu Ile Arg Lys Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Phe Phe Arg Lys Val Leu Lys Leu Ile Arg Lys Ile Phe
1               5                   10
```